US008715956B2

(12) United States Patent
Pruvost et al.

(10) Patent No.: US 8,715,956 B2
(45) Date of Patent: May 6, 2014

(54) METHOD FOR THE INTENSIVE EXTRACTION OF CELLULAR COMPOUNDS FROM MICRO-ORGANISMS BY CONTINUOUS CULTURE AND EXTRACTION, AND CORRESPONDING DEVICE

(75) Inventors: Jérémy Pruvost, Saint Brevin (FR); Jack Legrand, Saint Nazaire (FR); Alain Foucault, Saint Nazaire (FR)

(73) Assignees: Universite de Nantes, Nantes Cedex (FR); Centre National de la Recherche Scientifique (CNRS), Paris Cedex (FR)

( * ) Notice: Subject to any disclaimer, the term of this patent is extended or adjusted under 35 U.S.C. 154(b) by 526 days.

(21) Appl. No.: 12/597,863

(22) PCT Filed: Apr. 22, 2008

(86) PCT No.: PCT/EP2008/054869
§ 371 (c)(1),
(2), (4) Date: Mar. 1, 2010

(87) PCT Pub. No.: WO2008/135382
PCT Pub. Date: Nov. 13, 2008

(65) Prior Publication Data
US 2010/0178669 A1    Jul. 15, 2010

(30) Foreign Application Priority Data
Apr. 27, 2007   (FR) ...................................... 07 03070

(51) Int. Cl.
*C12P 1/00* (2006.01)
(52) U.S. Cl.
USPC .......................... 435/41; 435/289.1; 68/23 R
(58) Field of Classification Search
None
See application file for complete search history.

(56) References Cited

U.S. PATENT DOCUMENTS

| | | | |
|---|---|---|---|
| 5,110,319 A | 5/1992 | Turpin et al. | |
| 7,947,827 B2 * | 5/2011 | Bailey et al. | 540/145 |
| 2006/0191848 A1 | 8/2006 | Ruffer et al. | |

FOREIGN PATENT DOCUMENTS

| | | |
|---|---|---|
| EP | 1501937 A2 | 2/2005 |
| JP | 63105683 A | 5/1988 |
| WO | 03092853 A1 | 11/2003 |
| WO | 03095397 A2 | 11/2003 |

OTHER PUBLICATIONS

Molinari et al., Enzyme and Microbial Technology, 1997, vol. 20, p. 604-611.*
Hejazi et al., Biotechnology and Bioengineering, 2004, vol. 85, No. 5, p. 475-481.*
Oliver et al., J Chromatogr. A, 2000, vol. 881, p. 543-555.*
Tsai et al., "Measurement of Partition Coefficient Using Centrifugal Partition Chromatography", Modern Counter current Chromatography, American Chemical Society, ACS Symposium Series, Chapter 13, p. 143-154.*
Sutherland et al: "Recent Progress on the Industrial Scale-Up of Counter-Current Chromatography" Journal of Chromatography A, Elsevier, Amsterdam, NL, [Online] vol. 1151, No. 1-2, Mar. 1, 2007, pp. 6-13, XP022063764 ISSN:0021-9673 Retrieved from the Internet: URL: http://www.sciencedirect.com> [retrieved on Nov. 9, 2007] pp. 6-9.
Marchal L. et al: "Centrifugal Partition Chromatography: A Survey of its History, and our Recent Advances in the Field" Chemical Record, John Wiley, New York, NY, US, vol. 3, No. 3, 2003, pp. 133-143, XP002452497.
Database WPI Week 198824 Thomson Scientific, London, GB; AN 1988-166137, XP002499678 JP 63 105683 A (Shokuhim Sangyo Bioreactor) May 10, 1988 abstract.
International Search Report dated Oct. 24, 2008 for corresponding International Application No. PCT/EP2008/054869, filed Apr. 22, 2008.
Leon et al., "Microalgae mediated photoproduction of beta-carotene in aqueous-organic two phase systems." Dpt. de Química y CC MM (Area de Bioquímica), Facultad de Ciencias Experimentales, Campus del Carmen, Universidad de Huelva, 21071 Huelva, Spain. Biomol Eng. Jul. 20, 2003 (4-6): 177-82. Abstract.

* cited by examiner

*Primary Examiner* — Kade Ariani
(74) *Attorney, Agent, or Firm* — David D. Brush; Westman, Champlin & Koehler, P.A.

(57) ABSTRACT

A method is provided for extracting cellular compounds from micro-organisms. The method includes culturing the micro-organisms and extracting the cellular compounds from the micro-organisms. Each step is carried out in a continuous manner, wherein the extraction step is carried out separately from the culture step and in conditions of biocompatibility with the micro-organisms. The method further includes at least one step of recovering the cellular compounds and at least one step of recirculating the micro-organisms towards the culture step.

4 Claims, 2 Drawing Sheets

METHOD FOR THE INTENSIVE EXTRACTION OF CELLULAR COMPOUNDS FROM MICRO-ORGANISMS BY CONTINUOUS CULTURE AND EXTRACTION, AND CORRESPONDING DEVICE

CROSS-REFERENCE TO RELATED APPLICATIONS

This Application is a Section 371 National Stage Application of International Application No. PCTEP2008/054869, filed Apr. 22, 2008 and published as WO 2008/135382 on Nov. 13, 2008, not in English.

STATEMENT REGARDING FEDERALLY SPONSORED RESEARCH OR DEVELOPMENT

None.

THE NAMES OF PARTIES TO A JOINT RESEARCH AGREEMENT

None.

FIELD OF THE DISCLOSURE

The field of the disclosure is that of methods for the extraction of cellular compounds.

Various applications of the disclosure may be envisaged, particularly the extraction of:
  bioactive molecules (pigments, vitamins, etc.), for the fields of pharmaceuticals, cosmetics and food processing;
  high energy potential molecules (lipids) for the field of energy.
More specifically, the disclosure relates to a method and device for the intensive and biocompatible extraction of intracellular compounds from photosynthetic micro-organisms.

BACKGROUND OF THE DISCLOSURE

One of the benefits of photosynthetic micro-organisms such as microalgae and cyanobacteria lies in the original composition thereof.

However, the majority of these compounds involve the application of stress conditions to the culture so as to make use of the significant metabolic flexibility of this type of micro-organism to achieve the biosynthesis of the desired compound.

If this compound is intracellular (such as pigments in particular), it is necessary to implement a second extraction step which, in the majority of cases, causes irreversible damage to the culture (grinding, thermal or osmotic shock, cellular disintegration, etc.).

Therefore, industrial productions based on this principle use discontinuous productions, successively alternating biomass production, stress condition application phases, followed by harvesting, extraction and purification phases.

The main drawback of discontinuous productions is associated with the low growth rate of photosynthetic micro-organisms (compared to heterotrophic micro-organisms such as bacteria or yeasts), preventing frequent harvesting, or, at the very least, involving work with a plurality of production systems in parallel.

For some compounds, it is possible to implement an original extraction technique, wherein only the compound is extracted, without altering the cell significantly (biocompatible extraction). This enables the continuous production of the compound, while preventing the repetition of the growth and stress phase.

Indeed, if this technique is associated with continuous biomass production in a photobioreactor, once the initial growth phase has been carried out, the stress conditions subsequently applied can be theoretically maintained indefinitely, provided that the compound produced is continually extracted.

This results in a non-negligible gain in production compared to discontinuous methods, avoiding the losses associated with the latent period before obtaining a further biomass having the desired cellular composition.

Such a continuous production-extraction technique was proposed by Hejazi and Wijffels in 2003 (patent document published under the number EP-1 501 937) and is described with reference to FIG. 1.

This device is also based on the research detecting the existence of biocompatible solvents enabling the extraction of reusable compounds, in this instance β-carotene from the microalga *Dunaliella* salina (research by Leon et al., 2003).

As illustrated in FIG. 1, this device comprises a photobioreactor wherein the culture 1 containing the compound to be extracted and the solvent 2 wherein the compound is progressively extracted coexist (biphase system).

Although it is operational, this method displays various limitations. Indeed, the extraction rate remains relatively low, due to the difficulty placing the two non-miscible phases (cultures in aqueous medium and hydrophobic solvent) in contact. As the contact interface remains small, there is a significant resulting limitation in material transfer. The solution consists of mixing the whole very vigorously, which, however, rapidly reaches a limit determined by the fragility of the cultured cells.

A further drawback lies in the impossibility to impose optimal conditions, as both processes (biosynthesis and extraction) are different. For example, as extracted β-carotene is photosensitive, the use of strong lighting (stress condition required for biosynthesis) for culture makes it necessary to draw off the solvent charged with pigment regularly before degradation.

SUMMARY

An aspect of the disclosure relates to a method for the extraction of cellular compounds from micro-organisms, of the type that comprises:
  a culture step of said micro-organisms;
  an extraction step of said cellular compounds from said micro-organisms,
  characterised in that each step is carried out in a continuous manner, said extraction step being carried out separately from said culture step, and said extraction step being carried out under conditions of biocompatibility with said micro-organisms, followed by:
    at least one step for recovering said cellular compounds;
    at least one step for recirculating said micro-organisms towards said culture step.

In that the method is based on two separate and continuous cellular compound culture and extraction steps, an embodiment of the invention is applicable both to photosynthetic micro-organisms and to non-photosynthetic micro-organisms (bacteria, yeasts). Only the culture step differs, the photobioreactor (in the case of photosynthetic micro-organisms) possibly being replaced by any other bioreactor suitable for the micro-organism used.

Since each of the phases (production by means of culture and extraction) is based on very different principles, technologies and parameters, the operation in two subsystems according to an embodiment of the invention makes it possible to obtain an intensified overall method with the option of enhanced and independent control of each subsystem.

It should be noted that an embodiment of the invention is particularly applicable to the extraction of an intracellular compound. However, in some cases, the micro-organisms may release a metabolite (extracellular metabolite) in the medium. An embodiment of the invention is also applicable to this case, with the same overall operating principle, the only difference being that the metabolite is then extracted from the culture medium by the extractor (liquid-liquid extraction), instead of directly from the cell (solid-liquid extraction).

However, whether the metabolite is intra- or extra-cellular, the looped operating concept of both subsystems is only possible if the extraction phase is not destructive with respect to the biological material, so that the living cells are reintroduced into the production subsystem.

Otherwise, both subsystems operate in cascade, which is a conventional industrial format. Therefore, the extraction step should prevent irreversible damage to the culture, whether from mechanical, thermal or chemical causes. A suitable choice of the extraction system makes it possible to prevent mechanical damage and thermal shocks.

Therefore, the originality of an embodiment of the invention lies in the division into two optimised subsystems, operating in a coupled manner, each complying with the constraints eventually enabling continuous production-extraction. Compared to the existing system, two major benefits are provided:
- option to increase material transfers at the extractor (and therefore improved overall yield);
- option to apply different conditions for extraction than for production to preserve the integrity of the intracellular compound extracted.

In sum, an embodiment of the invention enables major improvements both with respect to material transfer and with respect to the option offered to apply optimal operating conditions for both steps (production and extraction), by implementing two subsystems dedicated for each step and operating in a coupled manner, i.e. with continuous production and under intracellular compound stress conditions, and a biocompatible extraction part with respect to said compound.

It should be noted that, even if, in principle, the complexity of the method is increased by the use of the two subsystems, the coupling is facilitated by the operation in continuous and permanent mode. It is thus possible to optimise the culture conditions to improve extraction (maintaining a constant intracellular concentration over time enables better definition of the extraction conditions to be applied).

According to one advantageous solution, said culture step is a bioproduction step, providing the live medium with the conditions required for the synthesis of the desired metabolite.

Advantageously, said extraction step is a liquid-liquid (extracellular metabolite) or solid-liquid (intracellular metabolite) extraction step.

Such an extraction mode ensures the transfer of the desired metabolite from the cell (case of an intracellular compound) and/or the culture medium (case of an exuded extracellular compound) to a solvent subsequently recovered at the extractor outlet.

According to a preferred solution, said extraction step is performed by means of Centrifugal Partition Chromatography (CPC).

In this way, the high transfer capacities of CPC make it possible to obtain a high-performance liquid-liquid extraction system.

However, the use of CPC involves a major constraint, i.e. the possibility of high mechanical stress subjected to the live cells while passing through the apparatus (centrifugal field, culture pumping system, shearing between and in each separation cell). Therefore, the system is only suitable for continuous use if the culture is capable of withstanding this treatment. Tests have demonstrated the feasibility of the approach and the potential thereof (increased yields with respect to the literature), subject, however, to remaining within an acceptable CPC operating range to preserve the integrity of the biological material.

According to one possible alternative embodiment, said extraction step is carried out protected from light.

According to a further possible alternative embodiment, said extraction step is carried out in anoxia in gaseous nitrogen.

Therefore, it is understood that a method according to an embodiment of the invention enables the ready application of the specific conditions in the extraction system, such as working protected from light if the product is photosensitive, or under anoxia conditions, if the product is oxidised rapidly. Similarly, the extraction mode adopted may be selected to achieve a high selectivity (choice of solvent and extraction time control).

An embodiment of the invention also relates to a device for the implementation of a method as described above, comprising:
- at least one vessel for the culture of said micro-organisms,
- at least one vessel for the extraction of said cellular compounds from said micro-organisms, said extraction vessel being separate from said culture vessel and containing at least one solvent biocompatible with said micro-organisms;
- means for recovering said cellular compounds;
- means for recirculating said micro-organisms from said extraction tank in said culture vessel.

It is noted that an embodiment of the invention prevents chemical damage to the micro-organisms, by using a biocompatible solvent, which extracts the intracellular metabolite, without altering the metabolism of the micro-organism irreversibly potentially leading to cellular lysis.

According to one advantageous solution, said culture vessel is a photobioreactor, and said extraction vessel is a liquid-liquid extraction vessel.

BRIEF DESCRIPTION OF THE DRAWINGS

Other features and advantages will emerge more clearly on reading the following description of a preferential embodiment of the invention, given as an illustrative and non-limitative example, and the appended figures, wherein.

DETAILED DESCRIPTION OF ILLUSTRATIVE EMBODIMENTS

As specified above, the principle of an embodiment of the invention lies in the provision of a method for the production-extraction of cellular compounds based on the association of two subsystems operating in a loop, each being specifically dedicated to either of the production or extraction phases.

Figure 1:
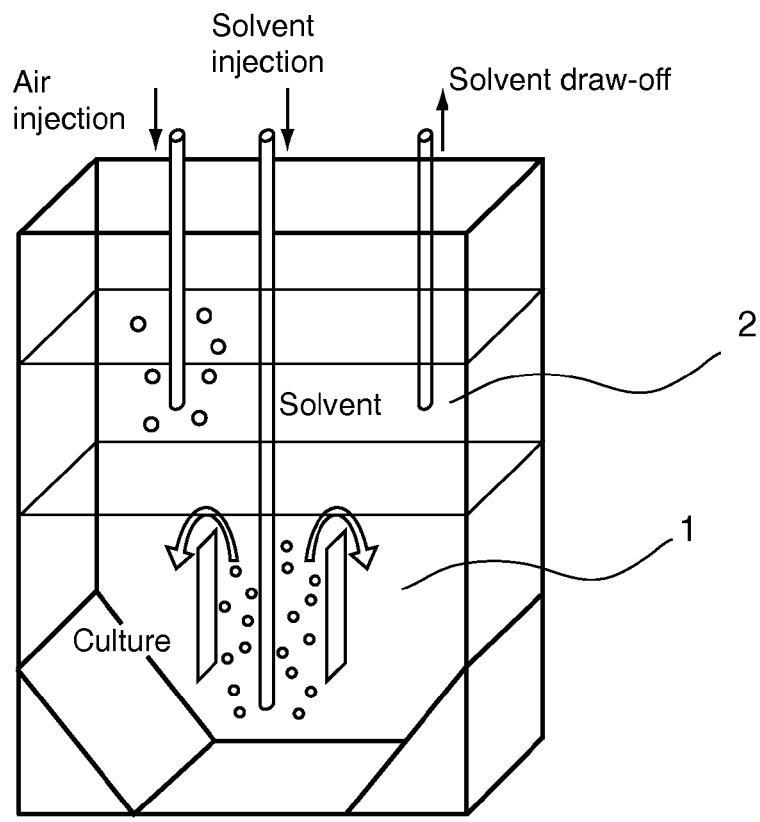
FIG. 1 is a schematic representation of an inventive production-extraction technique according to the prior art.
Figure 2:
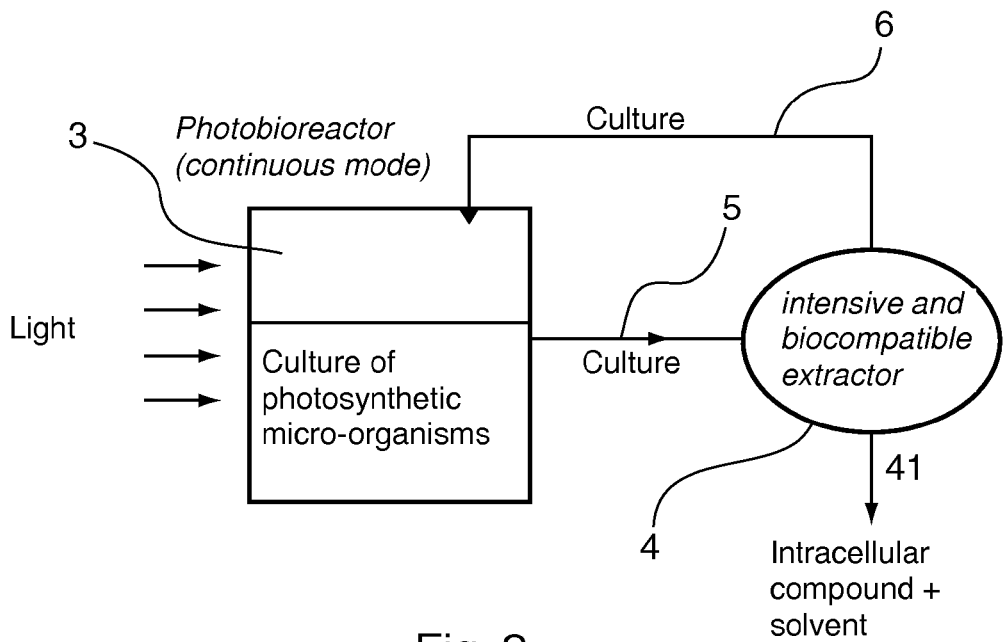
FIG. 2 is a schematic representation of a device for the implementation of a method according to an embodiment of the invention.

A device for the implementation of a method according to an embodiment of the invention is described with reference to FIG. 2.

Such a device comprises:
- a culture vessel (such as a photobioreactor) 3 operating in continuous mode carrying out the photosynthetic micro-organism culture step;
- an extractor 4 carrying out continuous extraction of the cellular compounds;
- means 5 for transferring the micro-organisms from the photobioreactor into the extractor 4;
- means 41 for recovering the cellular compounds;
- means 6 for recirculating the micro-organisms from the extractor 4 into the photobioreactor 3.

The biosynthesis phase is thus carried out in one or a plurality of photobioreactors operating continuously, enabling the application of ideal controlled conditions to achieve at an optimised biosynthesis rate of the desired compound. By modifying the physicochemical culture parameters (temperature, pH, culture medium, incident light), it is thus possible to promote, by inducing physiological stress, the biosynthesis of a specific metabolite, involved for example in protecting the micro-organism against said stress (example of β-carotene in a luminous and oxidative stress situation).

The extractor consists of a vessel containing a biocompatible solvent such as dodecane or decane.

With such a solvent, biocompatible extraction is performed. It is then possible to extract, in a continuous and selective manner, certain intracellular compounds while preserving cell vitality.

In the case of a slightly hydrophobic solvent, contact alters the cellular structure irremediably. In this case, extraction is very significant, but not selective (a large quantity of compounds are extracted) and not biocompatible.

On the other hand, if the solvent selected is sufficiently non-polar, the cell wall and vital functions thereof may be preserved, while maintaining extraction of certain hydrophobic compounds, particularly chlorophyll and β-carotene from *Dunaliella salina*. The greater the non-polarity of the solvent, the more the extraction capacity decreases, with a more marked reduction for chlorophyll. Therefore, by selecting a suitable solvent, biocompatible selective β-carotene extraction may be obtained.

Compared to conventional methods for the rough but quasi-complete extraction of intracellular pigments, the loss of productivity generated by the use of a highly non-polar solvent, which is in principle less effective, may be compensated by maintaining continuous extraction of β-carotene directly from cells in culture.

According to the principle of an embodiment of the invention, the solvent is maintained in a parallel system dedicated for extraction (the extractor 4, clearly physically separated from the photobioreactor 3) wherein the culture transits before returning to the production photobioreactor(s).

Such a device, and by applying significant percolation for example (the dispersed phase is the culture, and the continuous phase the solvent), results in a significant increase in the interfacial surface areas between the aqueous biological medium and the solvent (non-miscible phases). Although this induces high levels of mechanical stress (hydrodynamic stress), this is compensated by a short passage time in the extraction subsystem, in view of the high extraction rate.

According to a preferential embodiment, the extraction step is carried out by means of Centrifugal Partition Chromatography (CPC): comparable to HPLC (High-Performance Liquid Chromatography), this technique differs therefrom however in the absence of a solid substrate and the high processing capacity thereof.

In the CPC technique, the useful part consists of a rotating disk provided with a series of separation cells. By means of a strong centrifugal force field, one of the phases, referred to as the stationary phase, is maintained in the apparatus. The other phase (mobile phase) circulating with a forced flow rate then percolates into each cell in the stationary phase, resulting in a significant increase in the contact of both liquid phases. The efficiency is dependent on the operating conditions (rotation speed, mobile phase flow rate), the physical properties of both phases and the shape of each separation cell (Marchal 2001). This method is usually applied to purifications of molecules from complex mixtures: active natural compounds, peptides, fatty acids, phospholipids, antibiotics, aroma extraction, petroleum product fractionation, etc.

According to the target application, the use of large volume photobioreactors, culture tanks, or photobioreactors with smaller but intensified volumes may be envisaged. This will also apply to the extractor, which will be either a conventional liquid-liquid extraction column, or intensified extractors wherein material transfer and the contact of the culture medium with the extractor solvent are optimised (e.g. CPC).

Figure 3:
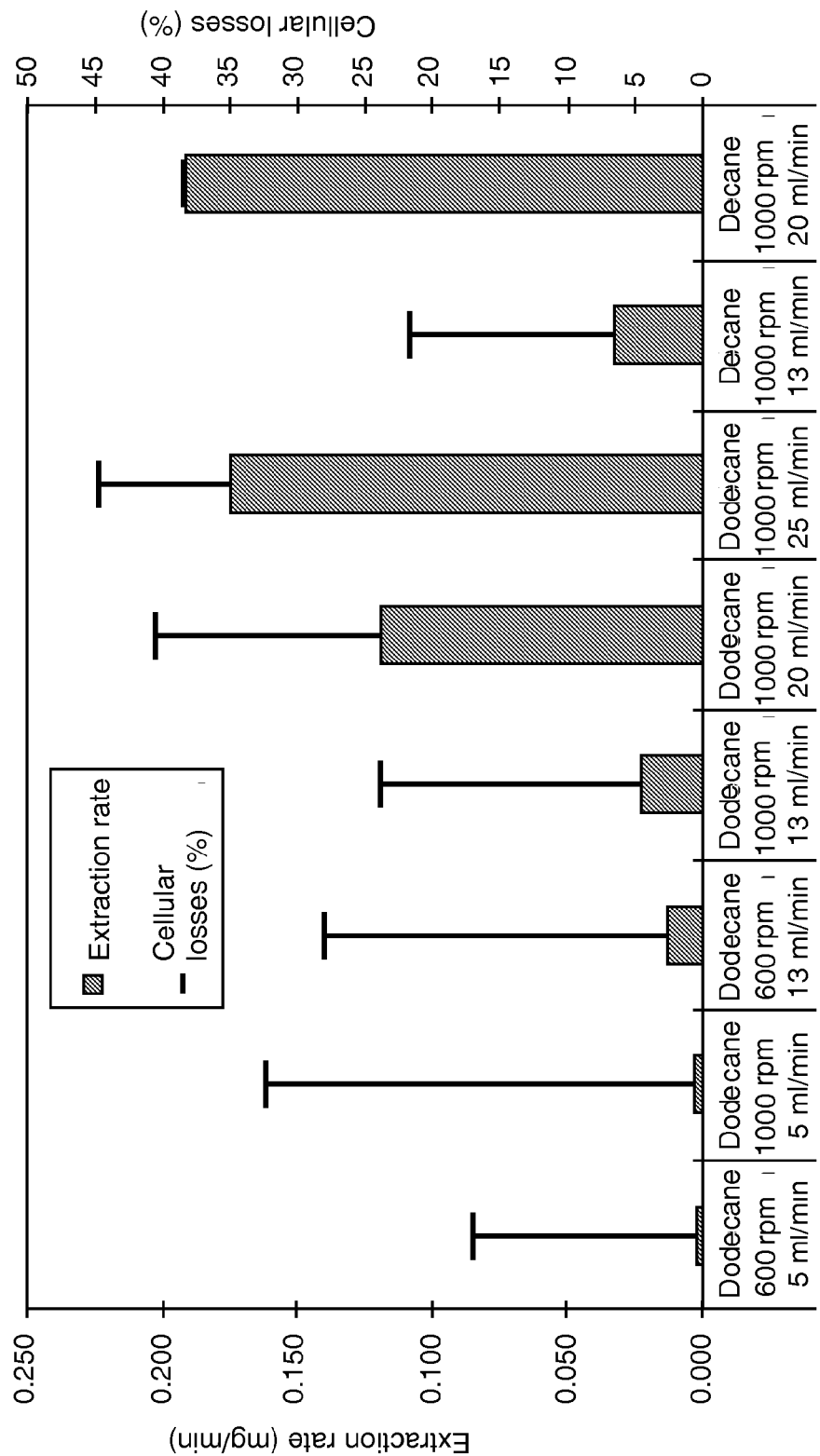
FIG. 3 is a graph demonstrating intracellular β-carotene CPC extraction results of a *Dunaliella* salina culture, using a method according to an embodiment of the invention.

To demonstrate the feasibility of the CPC-photobioreactor coupling, tests were conducted and were particularly intended to evaluate the quantity of β-carotene extracted and the associated cellular losses, as a function of various CPC operating parameters, using dodecane and decane as solvents. Some examples of results are given in FIG. 3.

These results highlight three of the main features of the method, i.e.:
- the vital role of material transfer during extraction;
- the need to find a compromise to retain cellular integrity and;
- the influence of the solubility of β-carotene in the solvent.

The mobile (culture) phase feed flow rate in CPC thus plays an important role. A higher quantity of β-carotene is extracted at a high flow rate, but with considerable damage to the living cells (loss of flagella, mortality).

Due to the ability of the live medium to regenerate, a slight loss of biomass is however acceptable. In this way, 48 hours after the passage in CPC under severe conditions, a large proportion of the culture is recovered (losses with respect to the initial concentration of 40% to 20%).

This demonstrates the diversity of the possible operating protocols, with either moderate but permanent extraction, or high but sequential extraction, with latent periods to be defined to regenerate the live material between each extraction.

It should be noted that these various operating options is no way modify and are covered in the overall principle of an embodiment of the invention described above (operation in two subsystems).

It should be noted that the separation of the two production and extraction steps enables optimisation of each of the phases (and the coupling thereof).

With respect to the production part, it is important to find the conditions enabling maximised intracellular β-carotene composition. These conditions must be kept in continuous operation. The CPC operating conditions can thus be optimised more readily.

Due to the innovation provided by the operation in two subsystems, various tests were carried out, so as to implement new specific protocols.

Indeed, the majority of the existing protocols were developed on the basis of extensive discontinuous culture.

Operation in a continuous photobioreactor offers a point of view to be optimised.

In this way, the intracellular concentration usually around 15-20 pg per cell was increased to 70.

This was obtained by means of physiological forcing by adjusting the conventional photobioreactor culture operating conditions (temperature, irradiance, pH) and by modifying the culture medium. Two compounds were thus added to the standard culture medium, i.e. acetate and iron ($Fe^{2+}$), both compounds enabling the promotion of both the growth and biosynthesis of β-carotene. It should be noted that operation in continuous culture mode enables easy optimisation of the respective quantity of each of the compounds (constant quantity per cell over time).

The association of CPC with a 4 liter single rectangular photobioreactor having a 3 cm optical path operating continuously where the conditions leading to β-carotene biosynthesis were applied made it possible to obtain initial results supporting the various improvements provided by each subsystem. In this way, the prior art studies conducted on β-carotene extraction in a single reactor demonstrated that not more than 5 to 10 mg/l could be extracted.

CPC made it possible to obtain 148 mg/l extraction of β-carotene at the column head, which is 30 times greater than the methods used according to the prior art (CPC extraction conditions; feed flow rate 20 ml/min—Rotation speed 1000 rpm—Solvent Decane; Culture conditions: 4-liter rectangular—pH 7.5—Temperature 30° C.—Salinity 220 g/l—Incident light 700 $\mu E/m^2.s$). In total, 1.25 mg of β-carotene was extracted for 3200 ml of culture and 60 ml of solvent.

In continuous production, a productivity of the order of 50 mg of carotenoids per day and liter of culture is expected.

An exemplary embodiment of the disclosure provides a technique for the continuous production-extraction of cellular compounds from micro-organisms making it possible to envisage increased production and extraction rates with respect to the techniques of the prior art.

An embodiment provides such a technique involving the application of specific operating conditions suitable for the extracted compounds, either to protect the properties thereof after extraction, or to improve the purity of the extracted compounds, by selective solvent selection and extraction time control.

An embodiment provides such a technique enabling the extraction of both intracellular compounds and extracellular compounds.

Although the present disclosure has been described with reference to one or more examples, workers skilled in the art will recognize that changes may be made in form and detail without departing from the scope of the disclosure and/or the appended claims.

The invention claimed is:

1. A method of extracting cellular compounds from a photosynthetic microorganism, which comprises:
    a step of culturing said photosynthetic microorganism in a photobioreactor to produce cellular compounds;
    an extraction step of said cellular compounds from said photosynthetic microorganism,
    wherein said culture and extraction steps are carried out in a continuous and parallel manner, said extraction step being carried out in an extraction vessel separately from said culture step, and wherein said extraction step is carried out by centrifugal partition chromatography, under conditions of biocompatibility with said photosynthetic micro-organism, using an apolar solvent comprising at least one of decane or dodecane, said solvent being maintained in said extraction vessel, and said extraction step being followed by:
    at least one step of recovering said cellular compounds; and
    at least one step of recirculating said photosynthetic microorganism towards said photobioreactor.

2. The method according to claim 1, wherein said culture step is carried out in a plurality of photobioreactors operating continuously.

3. The method according to claim 1, wherein said extraction step is carried out protected from light.

4. The method according to claim 1, wherein said extraction step is carried out in anoxia in gaseous nitrogen.

* * * * *

UNITED STATES PATENT AND TRADEMARK OFFICE
CERTIFICATE OF CORRECTION

PATENT NO. : 8,715,956 B2
APPLICATION NO. : 12/597863
DATED : May 6, 2014
INVENTOR(S) : Pruvost et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 845 days.

Signed and Sealed this
Twenty-ninth Day of September, 2015

Michelle K. Lee
*Director of the United States Patent and Trademark Office*